United States Patent

Swoyer et al.

[11] Patent Number: 5,954,759
[45] Date of Patent: Sep. 21, 1999

[54] FRACTURE RESISTANT MEDICAL ELECTRICAL LEAD

[75] Inventors: John M. Swoyer, Andover, Minn.; Annette Hebzynski, Mesa, Ariz.

[73] Assignee: Medtronic, Inc., Minneapolis, Minn.

[21] Appl. No.: 08/843,765

[22] Filed: Apr. 21, 1997

[51] Int. Cl.⁶ ..................................... A61N 1/05
[52] U.S. Cl. ............................................. 607/122
[58] Field of Search ..................... 607/116, 119, 607/122, 132

[56] References Cited

U.S. PATENT DOCUMENTS 3,474,791  10/1969  Bentov ..................................... 607/132
4,559,951  12/1985  Dahl et al. .

*Primary Examiner*—William E. Kamm
*Attorney, Agent, or Firm*—Reed A. Duthler; Harold R. Patton

[57] ABSTRACT

An implantable medical lead provided with a coiled conductor extending from a connector assembly at a proximal end of the lead to an electrode on the lead body and a stranded conductor extending from the connector assembly to a point distal thereto. The stranded conductor is coupled to the coiled conductor at both of its ends and provides both for an increased resistance to fracture of the coiled conductor and a redundant conductor in case the coiled conductor does fracture.

8 Claims, 2 Drawing Sheets

FRACTURE RESISTANT MEDICAL ELECTRICAL LEAD

BACKGROUND OF THE INVENTION

The present invention relates to implantable electrical leads generally, and more specifically to cardiac pacing leads.

The conductors in cardiac pacing leads generally, and in epicardial pacing leads in particular, occasionally have a tendency to fracture due to repetitive application of stress to the conductor. One way in which this problem has previously been addressed is by reinforcing the lead body in the area in which stress is to be expected, as in U.S. Pat. No. 5,545,203, issued to Doan et al. This patent is directed primarily toward reinforcing the lead against fracture due to application of compressive forces. Reinforcement of the lead body is also disclosed in U.S. Pat. No. 5,591,142, issued to Van Erp et al. It has also been proposed to reinforce the body by means of adding a tensile reinforcement as in U.S. Pat. No. 5,231,996 issued to Bardy et al. In this patent, the lead is provided with a non-conductive tensile member such as a Dacron cord, which runs the length of the lead body. Other leads having cords or reinforcements running throughout their length are disclosed in U.S. Pat. No. 3,844,292 and U.S. Pat. No. 3,574,344 issued to Bolduc. A third proposal for dealing with the possibility of conductor fracture is to render the portion of the lead body in direct contact with the conductor conductive by addition of carbon or other conductive material, as disclosed in U.S. Pat. No. 4,033,355, issued to Ammundson.

SUMMARY OF THE INVENTION

The present invention is directed toward providing a lead which both has an increased resistance to fracture, and has the capability of continued function after fracture of a conductor. The lead is provided with a coiled conductor which may be monofilar or multifilar and which extends the length of the lead, running from an electrical connector at the proximal end of the lead to an electrode at or near the distal end of the lead. In addition, the lead is provided with a stranded conductor, preferably taking the form of a cable or a bundled stranded wire, which extends from the connector to which the coil's conductor is coupled distally to a point along the lead body, located distal to the point of expected breakage of the coiled conductor. The distal end of the stranded conductor is electrically and mechanically coupled to the coiled conductor, rendering the coiled conductor inextensible over the length of the stranded conductor and providing for continued electrical connection to the electrode, in the event that the coiled conductor fractures intermediate the proximal and distal ends of the stranded conductor.

If the present invention is embodied in the form of an endocardial lead, then electrode assembly 24 and electrode 26 may be replaced by corresponding structure from any conventional endocardial pacing or defibrillation lead, including those described in U.S. Pat. No. 5,456,705 issued to Morris, U.S. Pat. No. 5,282,844 issued to Stokes, U.S. Pat. No. 5,144,960 issued to Mehra, and U.S. Pat. No. 5,014,696 issued to Mehra, all incorporated by reference herein in their entireties.

In the lead as illustrated, a stranded conductor is provided, located within the coiled conductor connecting electrode 26 to pin 24. The stranded conductor extends from point A, within connector pin 14, to point B, proximal to the distal end of the lead body. In the context of epicardial leads, experience has shown that fractures most commonly occur within this portion of the lead. However, in the context of an endocardial lead, the point of attachment B may be elsewhere along the lead body. Alternatively, in some embodiments, the pacing electrode at the distal end of the lead may itself serve as the point of attachment of the stranded conductor to the coiled conductor.

Figure 1:
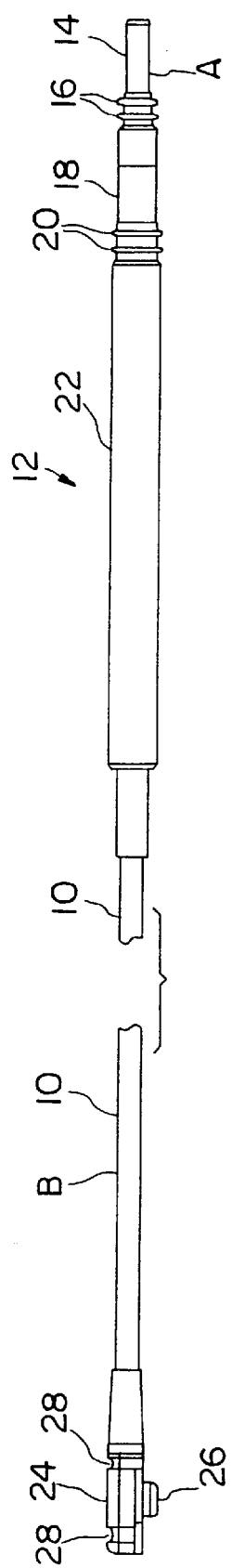
FIG. 1 shows a plan view of an epicardial lead employing the present invention. As illustrated, the lead is provided with an insulative elongated lead body 10 which carries a connector assembly 12 at its proximal end. The overall external configuration of the connector assembly as illustrated corresponds to the international "IS-1" connector standard, presently employed in conjunction with implantable cardiac pacing leads. At the proximal end of the connector assembly 12 is a connector pin 14 which is coupled by means of a coiled conductor extending through lead body 10 to an epicardial electrode 26. The connector assembly 12 also carries two sets of sealing rings 16 and 20 and a ring 18 which, in a unipolar embodiment as illustrated in FIG. 1, is unconnected to conductors within the lead. In the event the invention is practiced within the context of a bipolar embodiment, however, ring 18 would typically be a conductive ring, coupled to an additional conductor located within lead body 10 and extending to a second electrode. An insulative sleeve 22 is provided to ease the insertion of the lead into an implantable pacemaker or other stimulator and to provide strain relief at the point of lead exits the stimulator. At the distal end of the lead is an electrode assembly 24 which carries an epicardial electrode 26, which as illustrated is a steroid eluting epicardial electrode, but which may instead correspond to any of the numerous known epicardial or myocardial pacing electrodes or defibrillation electrodes, including those illustrated in U.S. Pat. No. issued to 5,443,492, issued to Stokes, U.S. Pat. No. 3,754,344 issued to Bolduc, U.S. Pat. No. 5,397,343 issued to Smits, U.S. Pat. No. 4,428,818 issued to Doring et al, U.S. Pat. No. 5,105,826 issued to Smits et al. and U.S. Pat. No. 4,817,634 issued to Holleman et al., all incorporated by reference in their entireties. Two suture grooves 28 are provided to assist suturing of the electrode head 24 to heart tissue.
Figure 2:
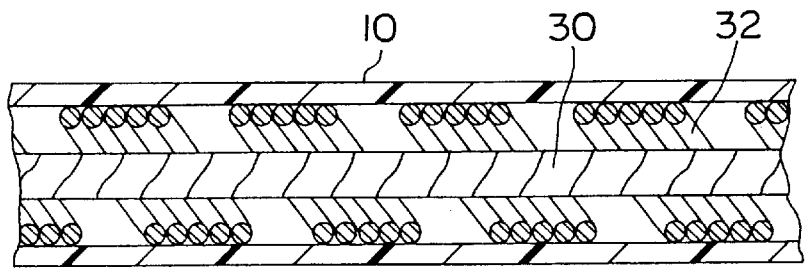

FIG. 2 illustrates a sectional view through the lead of FIG. 1, at a point intermediate the connector assembly and point B. In this view, stranded conductor 30 and coiled conductor 32 are visible, located within the insulative lead body 10. Coiled conductor 32 is illustrated as a multifilar coil, having five individual filars. However, the present invention may also be used in practice in conjunction with monofilar coils or multifilar coils having different numbers of filars. The stranded conductor 30 preferably takes the form of a cable conductor as described in U.S. Pat. No. 5,584,873 issued to Shoberg et al., incorporated herein by reference in its entirety or a bundled stranded wire conductor as disclosed in U.S. Pat. No. 5,246,014, issued to Williams et al, also incorporated by reference in its entirety. However, stranded or cabled conductors as disclosed in U.S. Pat. No. 4,964,414 issued to Handa, also incorporated herein by reference in its entirety, may also be substituted.

Figure 3:
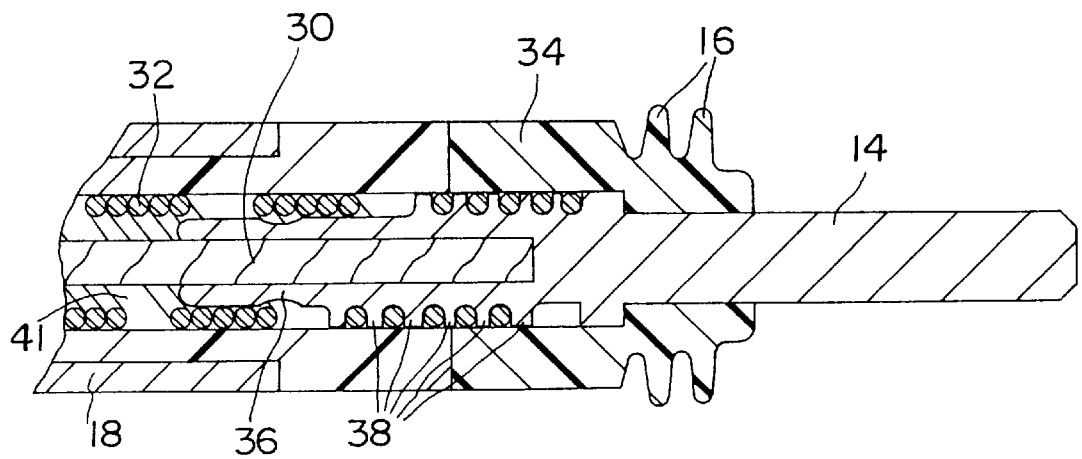

FIG. 3 illustrates one mechanism for interconnecting the coiled conductor 32, the stranded conductor 30 and the connector pin 14 in the connector assembly of the lead illustrated in FIG. 1. This method of interconnection corresponds generally to that disclosed in U.S. patent application, Ser. No. 08/657,577 filed by Boser et al. on Jun. 7, 1996, now U.S. Pat. No. 5,676,694 incorporated herein by reference in its entirety. In this commonly assigned, co-pending application, the interconnection mechanism is used to connect a stranded or cabled conductor to an exposed coiled electrode, rather than to an internal coiled conductor. Alternatively, coiled conductor 32 may be crimped directly to stranded conductor 30 by means of a cylindrical crimping sleeve surrounding coiled conductor 32 and compressing it against stranded conductor 30. Connector pin 14 is fabricated of stainless steel or other biocompatible metal and is provided with an internal lumen in which stranded conductor 30 has been inserted. Stranded connector 30 is retained within connector pin 14 by means of crimps 36. The distal portion of connector pin 14 is provided with external threads 38, in to which individual filars of conductor 32 are screwed. The filars of coil 32 are welded to the adjacent threads 38 on connector pin 14 to provide electrical and mechanical interconnection. Although not illustrated, volume 44 may be backfilled with medical adhesive or other resilient material to provide for stabilization of the connector assembly and for strain relief adjacent the distal end of connector pin 14. Ring 18 is also visible in cross-section, as are sealing rings 16, molded as part of an insulative polymeric sleeve 34, which is preferably fabricated of silicone rubber.

Figure 4:
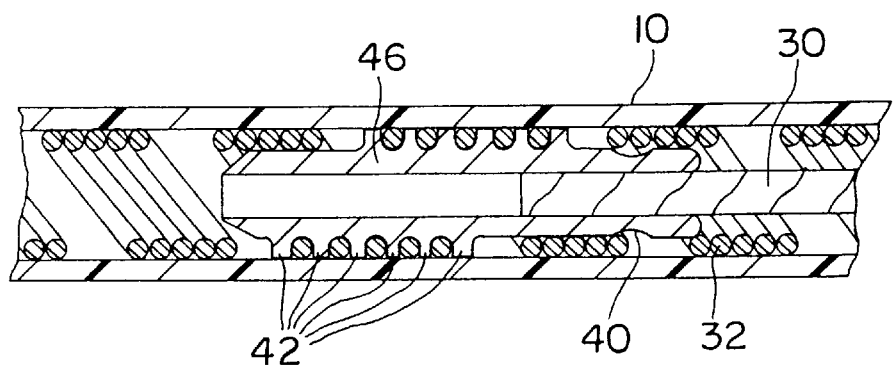

FIG. 4 illustrates the interconnection of the stranded conductor 30 to the coiled conductor 32 at point B, illustrated in FIG. 1. A conductive crimp/weld core 46, which may also be fabricated of stainless steel is provided with an internal lumen in which the distal end of stranded conductor 30 is located. Crimps 44 maintain stranded conductor 30 in mechanical and electrical engagement with core 46. Core 46 is also provided with external threads 32, corresponding to threads 38 in FIG. 3, and the individual filars of conductor 32 are welded to the adjacent threads 42 in the manner discussed above in connection with FIG. 3 to provide electrical and mechanical interconnection. Alternatively, coiled conductor 32 may be crimped directly to stranded conductor 30 by means of a cylindrical crimping sleeve surrounding coiled conductor 32 and compressing it against stranded conductor 30. In the event that it is desired that the point of interconnection of the coiled conductor 32 and the stranded conductor 30 be located at the distal, pacing electrode, core 46 may take the form of the proximal portion of the electrode, whereby stranded conductor 30 may extend the entire length of the lead.

While FIGS. 3 and 4 show one method of interconnection of stranded conductor 30 with coiled conductor 32, other mechanisms for connecting these types of conductors, known to the art, may also be substituted. For example, rather than welding conductor 32 to the core or connector pin, it may be engaged on the outer surface of the connector pin or core by means of a circumferential crimping sleeve. Similarly, rather than crimping stranded conductor 30 within core 46 or pin 14, it might instead be crimped within a welding sleeve, and the welding sleeve thereafter welded to either the connector pin or the core. Any interconnection mechanism is believed suitable as long as it provides electrical and mechanical interconnection.

The above disclosed lead takes the form of a unipolar epicardial lead. However, as discussed above, the basic invention set forth herein is believed applicable in the context of endocardial leads as well. Similarly, multi-conductor leads, having two, three or more conductors may also beneficially employ this invention, and the addition of additional conductors to a lead otherwise as described herein is believed within the scope of the invention. The above-illustrated embodiment should thus be considered exemplary, rather than limiting with regard to the claims that follow.

We claim:

1. An implantable electrical lead, comprising:
   an elongated, insulative lead body;
   an electrical connector located adjacent a proximal end of the lead body;
   an electrode located on the lead body distal to the electrical connector:
   a coiled conductor extending from the electrical connector to the electrode, located within the elongated, insulative lead body and mechanically and electrically coupled to both the connector and the electrode; and
   an elongated stranded conductor, electrically and mechanically coupled to the electrical connector and electrically and mechanically coupled to the coiled conductor at a point distal to the electrical connector.

2. A lead according to claim 1 wherein the stranded conductor is coupled to the coiled conductor at a point proximal to the electrode.

3. A lead according to claim 1 wherein the electrode is an epicardial electrode.

4. A lead according to claim 1 or claim 2 or claim 3 wherein said stranded conductor terminates at a point proximal to the electrode.

5. A lead according to claim 4 wherein the coiled conductor is a multi-filar coil.

6. A lead according to claim 4 wherein said stranded conductor comprises multiple strands.

7. A lead according to claim 1 or claim 2 or claim 3 wherein said coiled conductor is a multi-filar coiled conductor.

8. A lead according to claim 7 wherein said stranded conductor comprises multiple strands.

* * * * *